US009011906B2

(12) United States Patent
Najarian et al.

(10) Patent No.: US 9,011,906 B2
(45) Date of Patent: *Apr. 21, 2015

(54) ESCALATING DOSING REGIMEN FOR EFFECTING WEIGHT LOSS AND TREATING OBESITY

(71) Applicant: Vivus, Inc., Mountian View, CA (US)

(72) Inventors: Thomas Najarian, Los Osos, CA (US); Peter Y. Tam, Redwood City, CA (US); Leland F. Wilson, Menlo Park, CA (US)

(73) Assignee: Vivus, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/495,250

(22) Filed: Sep. 24, 2014

(65) Prior Publication Data

US 2015/0010626 A1 Jan. 8, 2015

Related U.S. Application Data

(63) Continuation of application No. 14/048,416, filed on Oct. 8, 2013, now Pat. No. 8,895,057, which is a continuation of application No. 12/481,548, filed on Jun. 9, 2009, now Pat. No. 8,580,299, which is a continuation-in-part of application No. 12/135,953, filed on Jun. 9, 2008, now abandoned.

(51) Int. Cl.
| | |
|---|---|
| *A61K 9/48* | (2006.01) |
| *A61K 31/357* | (2006.01) |
| *A61K 31/137* | (2006.01) |
| *A61K 31/35* | (2006.01) |
| *A61K 9/16* | (2006.01) |
| *A61K 9/50* | (2006.01) |
| *A61K 31/00* | (2006.01) |
| *A61K 31/135* | (2006.01) |
| *A61K 31/7048* | (2006.01) |
| *A61K 47/38* | (2006.01) |

(52) U.S. Cl.
CPC ............ *A61K 31/357* (2013.01); *A61K 31/137* (2013.01); *A61K 31/35* (2013.01); *A61K 9/167* (2013.01); *A61K 9/1676* (2013.01); *A61K 9/4866* (2013.01); *A61K 9/5026* (2013.01); *A61K 9/5047* (2013.01); *A61K 9/5073* (2013.01); *A61K 9/5084* (2013.01); *A61K 31/00* (2013.01); *A61K 31/135* (2013.01); *A61K 31/7048* (2013.01); *A61K 9/1629* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,513,006 | A | 4/1985 | Maryanoff et al. |
| 4,792,569 | A | 12/1988 | Maryanoff et al. |
| 4,895,845 | A | 1/1990 | Seed |
| 5,242,391 | A | 9/1993 | Place |
| 5,242,942 | A | 9/1993 | Costanzo et al. |
| 5,266,591 | A | 11/1993 | Wierzbicki et al. |
| 5,273,993 | A | 12/1993 | Lo et al. |
| 5,384,327 | A | 1/1995 | Costanzo et al. |
| 5,474,535 | A | 12/1995 | Place et al. |
| 5,498,629 | A | 3/1996 | Costenzo et al. |
| 5,527,788 | A | 6/1996 | Svec et al. |
| 5,543,405 | A | 8/1996 | Keown et al. |
| 5,753,693 | A | 5/1998 | Shank |
| 5,753,694 | A | 5/1998 | Shank |
| 5,773,020 | A | 6/1998 | Place et al. |
| 5,795,895 | A | 8/1998 | Anchors |
| 5,885,616 | A | 3/1999 | Hsiao et al. |
| 5,900,418 | A | 5/1999 | Viner |
| 6,071,537 | A | 6/2000 | Shank |
| 6,201,010 | B1 | 3/2001 | Cottrell |
| 6,319,903 | B1 | 11/2001 | Carrazana et al. |
| 6,323,236 | B2 | 11/2001 | McElroy |
| 6,362,220 | B1 | 3/2002 | Cottrell |
| 6,620,819 | B2 | 9/2003 | Marcotte |
| 6,627,653 | B2 | 9/2003 | Plata-Salaman et al. |
| 6,686,337 | B2 | 2/2004 | Connor |
| 6,908,902 | B2 | 6/2005 | Plata-Salaman et al. |
| 7,056,890 | B2 * | 6/2006 | Najarian ..................... 514/23 |
| 7,109,174 | B2 | 9/2006 | Plata-Salaman et al. |
| 7,109,198 | B2 | 9/2006 | Gadde et al. |
| 7,351,695 | B2 | 4/2008 | Almarssoo et al. |

(Continued)

FOREIGN PATENT DOCUMENTS

| | | |
|---|---|---|
| CA | 2377330 A1 | 12/2000 |
| CA | 2686633 A1 | 12/2000 |

(Continued)

OTHER PUBLICATIONS

"An Open Letter (Email) to Lazard." VivusPatent Wordpress. Sep. 6, 2013. Web. Sep. 13, 2013. http://vivuspatent.wordpress.com/2013/09/06/an-open-letter-email-to-lazard/.
FDC Reports, Inc. "Appetite Suppression Drugs Excluded by 81% of Employers—PBMI Survey." The Green Sheet, 48.19:3 (1999).
"Cowen's Response is Inadequate & Incomplete." VivusPatent Wordpress. Jul. 21, 2012. Web. Sep. 13, 2013. http://vivuspatent.wordpress.com/2012/07/21/cowens-response-is-inadequate-incomplete/.
"Daniel B. Ravicher's Response to Qsymia Patent Report: Why Reasonable People Hate Ethically-Challenged Lawyers." VivusPatent Wordpress. Aug. 4, 2012. Web. Sep. 13, 2013. http://vivuspatent.wordpress.com/2012/08/04/daniel-b-ravichers-response-to-qsymia-patent-report-why-reasonable-people-hate-ethically-challenged-lawyers/.
"Drug Therapies: Fastin, Ionamin (Phentermine)." Planet RD, Inc. (1999):3-4. www.obesity.com.

(Continued)

*Primary Examiner* — Hasan Ahmed
(74) *Attorney, Agent, or Firm* — Cooley LLP; Ivor R. Elrifi; Matthew Pavao

(57) ABSTRACT

The present invention is drawn to novel topiramate compositions as well as methods for effecting weight loss, e.g., in the treatment of obesity and related conditions, including conditions associated with and/or caused by obesity per se. The present invention features an escalating dosing regimen adapted for the administration of topiramate and optionally a sympathomimetic agent such as phentermine or bupropion, in the treatment of obesity and related conditions.

31 Claims, 2 Drawing Sheets

(56) References Cited

U.S. PATENT DOCUMENTS

| | | | |
|---|---|---|---|
| 7,429,580 B2 | 9/2008 | Gadde et al. | |
| 7,553,818 B2 | 6/2009 | Najarian | |
| 7,659,256 B2 | 2/2010 | Najarian | |
| 7,674,776 B2 * | 3/2010 | Najarian | 514/23 |
| 8,580,298 B2 * | 11/2013 | Najaraian et al. | 514/23 |
| 8,580,299 B2 * | 11/2013 | Najarian et al. | 424/451 |
| 8,895,057 B2 | 11/2014 | Najarian et al. | |
| 8,895,058 B2 | 11/2014 | Najarian et al. | |
| 2003/0072802 A1 | 4/2003 | Cutler | |
| 2004/0002462 A1 | 1/2004 | Najarian | |
| 2004/0122033 A1 | 6/2004 | Nargund et al. | |
| 2005/0032773 A1 | 2/2005 | Piot-Grosjean et al. | |
| 2005/0065190 A1 * | 3/2005 | Hinz | 514/350 |
| 2006/0058293 A1 | 3/2006 | Weber et al. | |
| 2006/0234950 A1 | 10/2006 | Najarian | |
| 2007/0129283 A1 * | 6/2007 | McKinney et al. | 514/2 |
| 2008/0085306 A1 | 4/2008 | Nangia et al. | |
| 2008/0103179 A1 | 5/2008 | Tam et al. | |
| 2008/0118557 A1 | 5/2008 | Liang et al. | |
| 2008/0255093 A1 | 10/2008 | Tam et al. | |
| 2009/0304785 A1 | 12/2009 | Najarian et al. | |
| 2009/0304789 A1 | 12/2009 | Najarian et al. | |
| 2010/0105765 A1 | 4/2010 | Najarian | |
| 2010/0215739 A1 | 8/2010 | Najarian et al. | |
| 2011/0262535 A1 | 10/2011 | Najarian et al. | |

FOREIGN PATENT DOCUMENTS

| | | | |
|---|---|---|---|
| CA | 2727313 A1 | 12/2009 | |
| WO | WO 00/50020 A2 | 8/2000 | |
| WO | WO 00/76493 A1 | 12/2000 | |
| WO | WO 2005/063206 A1 | 7/2005 | |
| WO | WO 2006/063078 * | 6/2006 | A61K 9/22 |
| WO | WO-2006/071740 A2 | 7/2006 | |
| WO | WO 2006/088748 A2 | 8/2006 | |
| WO | WO 2006/124506 A2 | 11/2006 | |
| WO | WO 2007/084290 A2 | 7/2007 | |
| WO | WO 2008/050020 A1 | 5/2008 | |
| WO | WO 2008/060963 A2 | 5/2008 | |
| WO | WO 2008/153632 A2 | 12/2008 | |
| WO | WO 2008/156550 A2 | 12/2008 | |
| WO | WO 2009/061436 A1 | 5/2009 | |
| WO | WO 2011/085256 A2 | 7/2011 | |

OTHER PUBLICATIONS

"Email to Mintz Levin re: 2007 Vivus Conference Call <http://vivuspatent.wordpress.com/2013/11/08/email-to-mintz-levin-re-2007-vivus-conference-call/>" VivusPatent World Press. Nov. 8, 2013. Web. Nov. 8, 2013. http://vivuspatent.wordpress.com/2013/11/08/email-to-mintz-levin-re-2007-vivus-conference-call/.
"FASTIN (Phentermine HCl) Capsules." U.S. Food and Drug Administration. Drug Labeling Changes. (1997). www.fda.gov/medwatch/safety/1997/oct97.htm.
"Intellectual Property Diligence for Vivus' Obesity Drug Qsymia." VivusPatent Wordpress. Jul. 20, 2012. Web. Sep. 13, 2013. http://vivuspatent.wordpress.com/2012/07/20/intellectual-property-diligence-for-vivus-obesity-drug-qsymia/.
"Ionamin (phentermine resin) Capsules." U.S. Food and Drug Administration. (1998). www.fda.gov/medwatch/safety/1998/feb98.htm.
"McElroy FTO—My Bad." VivusPatent Wordpress. Jul. 22, 2012. Web. Sep. 13, 2013. http://vivuspatent.wordpress.com/2012/07/22/mcelroy-fto-my-bad/.
"Memorandum from Division of Metabolism and Endocrinology Products (DMEP)." Department of Health and Human Services. May 22, 2007.
"Phentermine Hydrochloride." Physicians' Desk Reference. Montvale, NJ: Medical Economics Data Production Company. (1995):2508-2509.
"Phentermine." Physicians' Desk Reference. (1999):1053-1054.
"Sibutramine." The Merck Index, 13 Edition, No. 8559:1522 (2001).
"Two New Issued Qsymia Patents: Where Does Vivus Stand Now.?" VivusPatent Wordpress. Nov. 14, 2013. Web. Nov. 15, 2013. http://vivuspatent.wordpress.com/2013/11/14/two-new-issued-qsymia-patents-where-does-vivus-stand-now/.
"Vivus Qsymia Patents: Appearance of Ongoing and Systematic Inequitable Conduct before the USPTO by Vivus and its Attorneys." VivusPatent Wordpress. Aug. 12, 2013. Web. Sep. 13, 2013. http://vivuspatent.wordpress.com/2013/08/12/159.
"Vivus Qsymia Patents: Intellectual Property House of Cards." VivusPatent Wordpress. Aug. 8, 2013. Web. Sep. 13, 2013. http://vivuspatentwordpress.com/2013/08/08/vivus-qsymia-patents-intellectual-property-house-of-cards/.
"Wisdom From the Vivus Message Board." VivusPatent Wordpress. Aug. 5, 2012. Web. Sep. 13, 2013. http://vivuspatent.wordpress.com/2012/08/05/wisdom-from-the-vivus-message-board/.
Alger et al. "Effect of Phenylpropanolamine on Energy Expenditure and Weight Loss in Overweight Women", Am. J. Clin., 57:120-126 (1993).
Allen. "Methylcellulose." Handbook of Pharmaceutical Excipients. Web. (Jan. 2000).
Barcena et al. "Diagnosis and Treatment of Sleep Apnea in Heart Disease." Curr. Treat. Opt. Cardiovasc. Med. 9.6:501-509 (2007).
Barry et al. "Presurgical Electroencephalographic Patterns and Outcomes From Anterior Temporal Lobectomy." Arch. Neurol. 49:21-27 (1992).
Barth. "Cannabinoid Receptor Agonists and Antagonists." Exp. Opin. Ther. Patents. 8.3:301-313 (1998).
Bootsma et al. "Topiramate in Clinical Practice: Long-Term Experience in Patients with Refractory Epilepsy Referred to a Tertiary Epilepsy Center." Epilepsy Behavior. 5:380-387 (2004).
Bradley et al. "Bupropion SR with Phentermine for Weight Reduction." Book of Abstracts, American Psychiactric Association Meeting (distributed to meeting attendees). Washington, D.C.(1999). (Abstract Only).
Bray et al. "Current and Potential Drugs for Treatment of Obesity." Endocrine Rev. 20.6:805-875 (1999).
Bray et al. "Pharmacological Treatment of the Overweight Patient." Pharmaco. Rev. 59.2:151-184 (2007).
Bray et al. "Topiramate Produces Dose-Related Weight Loss." 62nd Annual American Diabetes Association Meeting. San Francisco, CA. (2002).
Campbell et al. "Pharmacologic Options for the Treatment of Obesity." Am. J. Health-Syst. Pharm. 58:1301-1308 (2011).
Carek et al. "Current Concepts in the Pharmacological Management of Obesity." Drugs. 6:883-904 (1999).
Citation filed by a third party in European Application No. 09763479.4 dated Nov. 6, 2013.
Citation filed by a third party in European Application No. 09763480.2 dated Nov. 6, 2013.
Communication pursuant to Rule 114(2) EPC issued in European Application No. 070114723 dated Aug. 9, 2013.
Communication pursuant to Rule 114(2) EPC issued in European Application No. 09763479.4 dated Nov. 14, 2013.
Communication pursuant to Rule 114(2) EPC issued in European Application No. 09763480.2 dated Nov. 14, 2013.
Coyne. Letter from Medeva Pharmaceuticals. (1997). www.fds.gov/medwatch/safety/1997/ionami2.htm.
Dahl. "Ethylcellulose." Handbook of Pharmaceutical Excipients. Web. (Jan. 2000).
Després et al. "Effects of Rimonabant on Metabolic Risk Factors in Overweight Patients with Dyslipidemia." New Eng. J. Med. 353:2121-2134 (2005).
European Communication issued in European Application No. 00939884.3 mailed May 25, 2004.
Exhibit 99.1: Conference Call Transcript from Nov. 9, 2007 regarding VVUS—Q3 2007 Vivus Earnings Conference Call. http://yahoo.brand.edgar-online.com/displayfilinginfo.aspx?FilingID=5538387-6827-59035&type=sect&tabindex=2&CompanyID=3684.
Faught et al. "Topiramate Dose-Ranging Trail in Refractory Partial Epilepsy." Epilepsia. 36.S4:33 (1995). (Abstact #D9).
Faught et al. "Topiramate Placebo-Controlled Dose-Ranging Trial in Refractory Partial Epilepsy Using 200-, 400-, and 600-mg Daily Dosages." Neurology. 46:1684-1690 (1996).
FDA: Memorandum from Division of Metabolism and Endocrinology Products (May 22, 2007).

(56) References Cited

OTHER PUBLICATIONS

Gadde et al. "A 24-Week Randomized Controlled Trial of VI-0521, a Combination Weight Loss Therapy, in Obese Adults." Obesity. 14.S:A17-A18. (2006) (Abstract #55-OR).
Gadde et al. "Bupropion SR in Obesity: A Randomized Double-Blind Placebo-Controlled Study." Obesity Res. 7.S1:51F. (1999) (Abstract #0136).
Gadde et al. "Cannabinoid-1 Receptor Antagonist, Rimonabant, for Management of Obesity and Related Risks." Circulation. 114:974-984 (2006).
Gadde et al. "Combination Therapy of Zonisamide and Bupropion for Weight Reduction in Obese Women: A Preliminary, Randomized, Open-Label Study." J. Clin. Psychiatry. 68.8:1226-1229 (2007).
Gadde et al. "Effects of Low-Dose, Controlled-Release, Phentermine Plus Topiramate Combination on Weight and Associated Comorbidities in Overweight and Obese Adults (CONQUER): A Randomised, Placebo-Controlled, Phase 3 Trial." Lancet. 377:1341-1352 (2011).
Garvey et al. "Two-Year Sustained Weight Loss and Metabolic Benefits with Controlled-Release Phentermine/Topiramate in Obese and Overweight Adults (SEQUEL): A Randomized, Placebo-Controlled, Phase 3 Extension Study." Am. J. Clin. Nutr. (2011).
Glauser. "Topiramate." Epilepsia. 40.S5:S71-S80 (1999).
Glazer et al. "Long-Term Pharmacotherapy of Obesity 2000." Arch. Intern. Med. 161.15:1814-1824 (2001).
Goldberg et al. "Lithium Treatment of Bipolar Affective Disorders Under Naturalistic Followup Conditions." Psychopharmacol. Bull. 32.1:47-54 (1996).
Greenway et al. "Bupropion and Zonisamide for the Treatment of Obesity." Obesity. 14.S:A17 (2006). (Abstract #52-OR).
Griffen et al. "The 'phen-pro' Diet Drug Combination is not Associated with Valvular Heart Disease." Arch. Intern. Med. 158.11:1278-1279 (1998).
Hillard et al. "Synthesis and Characterization of Potent and Selective Agonists of the Neuronal Cannibinoid Receptor (CB1)." J. Pharmacol. Exp. 289.3:1427-1433 (1999).
Hobbs. "Vivus' Qnexa Phase 2 Study Results Demonstrate Significant Weight Loss and Reduction in Waist Circumference." Medical News Today. (2006). www.medicalnewstoday.com/articles/54854.php.
Hobbs. "Qnexa: Phentermine-Topriamate Drug Combo Causes Half of Patients to Lose an Average of 25 Pounds." Fatnews.com May 12, 2006. Retrieved Dec. 17, 2012. fatnews.com/index.php/weblog/comments/qnexa-[hentermine-topriamate-drug-combo-causes-half-of-patients-to-lose-an-average-of-24-pounds.htm.
Jallon et al. "Bodyweight Gain and Anticonvulsants." Drug Safety. 24.13:969-978 (2011).
Kaplan. "Pharmacological Therapies for Obesity." Gastroenterol. Clin. N. Am. 34:91-104 (2005).
Kibbe. "Povidone." Handbook of Pharmaceutical Excipients. Web. (Jan. 2000).
Kitagawa. "Treatment of Cluster Headache." Prog. Med. Sci. 215. 14(2005):1132-1136. (Japanese Original, No English Translation Available).
Korean Topiramate Study Group. "Low Dose and Slow Titration of Topiramate as Adjunctive Therapy in Refractory Partial Epilepsies: A Multicentre Open Clinical Trial." Seizure. 11:255-260 (2002).
Left. "Vivus (NASDAQ: VVUS): Why FDA Approval is not the Prescription." Citron Research. Jul. 19, 2012. Web. Sep. 13, 2013. <http://www.citronresearch.com/vivus-why-fda-approval-is-not/>.
Makriyannis et al. "Therapeutic Opportunities Through Modulation of the Endocannabinoid System." Neuropharmacol. 48:1068-1071 (2005).
Masand. "Weight Gain Assocaited with Psychotropic Drugs." Exp. Opin. Pharmacotherapy. 1.3:377-389 (2000).
McElroy et al. "Topiramate in the Treatment of Binge Eating Disorder Associated With Obesity: A Randomized Placebo-Controlled Trial." Am. J. Psych. 160.2:255-261 (2003).
Michelucci et al. "The Preclinical and Therapeutic Activity of the Novel Anticonvulsant Topiramate." CNS Drug Rev. 4.2:165-186 (1998).

Murray et al. "Global Mortality, Disability, and the Contribution of Risk Factors: Global Burden of Disease Study." Lancet. 349:1436-1442 (1997).
NIH. "Clinical Guidelines on the Identification, Evaluation, and Treatment of Overweight and Obesity in Adults." NIH Publication No. 98-4083. (Sep. 1998).
Onuma et al. "A Late Phase-II Clinical Study of Topiramate (KW-6485) in Refractory Epilepsy." J. New. Rem. Clin. 56.10:1659-1681 (2007). (Japanese Original and English Abstract).
Partial International Search Report (Invitation to Pay Fees) issued in International Application No. PCT/US2008/005549 mailed Nov. 12, 2008.
Penovich et al. "Weight Loss in Patients Receiving Topiramate for Intractable Epilepsy." Neurology. 44.S2 (1994). (Abstract #309P).
Pi-Sunyer et al. "A Review of Long-Term Studies Evaluating the Efficacy of Weight Loss in Ameliorating Disorders Associated with Obesity." Clin. Ther. 18.6:1006-1035 (1996).
Pi-Sunyer et al. "Effect of Rimonabant, a Cannabinoid-1 Receptor Blocker, on Weight and Cardiometabolic Risk Factors in Overweight or Obese Patients: RIO-North America: A Randomized Controlled Trial." JAMA. 295.7:761-775 (2006).
Potter et al. "Sustained Weight Loss Associated with 12-Month Topiramate Therapy." Epilepsia. 38.S8:97 (1997).
Privitera, "Topiramate: A new antiepileptic drug", Annals of Pharmacotherapy, 31.10:1164-1173 (1997).
Raritan. "Clinical Development of Topiramate of Obesity Extended to Simplify Dosing, Improve Tolerability." Johnson & Johnson Pharmaceutical Research & Development. (2002). www.jnj.com/news/finance/448.htm.
Ravicher. "Report Raising Vivus Qsymia Patent Infringement Concerns was not Competent." Seeking Alpha. Jul. 31, 2013. Web. Sep. 13, 2013. <http://seekingalpha.com/article/765111-report-raising-vivus-qsymia-patent-infringement-concerns-was-not-competent?source=feed>.
Reaven. "Role of Insuline Resistance in Human Disease (Syndrome X): An Expanded Definition." Annu. Rev. Med. 44:121-131 (1993).
Rosenstock et al. "A Randomized, Double-Blind, Placebo-Controlled, Multicenter Study to Assess the Efficacy and Safety of Topiramate Controlled Release in the Treatment of Obese Type 2 Diabetic Patients." Diabetes Care. 30.6:1480-1486 (2007).
Sachdeo et al. "Topiramate: Clinical Profile in Epilepsy." Clin. Pharmacokinet. 34.5:335-346 (1998).
Sachdeo et al. "Topiramate: Double-Blind Trial as Monotherapy." Epilespia. 36.S4:33 (1995). (Abstract #D8).
Shapira, et al., "Treatment of Binge-Eating Disorder with Topiramate: A Clinical Case Series", Journal of Clinical Psychiatry, 61.5:368-372 (2000).
Smith, P. et al., "Weight loss in moderately obese patients with sleep apnea", Ann. Intern. Med. 103.6, pt 1:850-855 (1985) (Abstract only).
Strejan et al. "Suppression of Chronic-Relapsing Experimental Allergic Encephalomyelitis in Strain-12 Guinea Pigs by Administration of Liposome-Associated Myelin Basic Protein." J. Neuroimmunol. 7:27-41 (1984).
Sussman et al. "Anterior Thalamic Stimulation in Medically Intractable Epilepsy. Part II: Preliminary Clinical Results." Epilepsia. 29.5:677 (1988). (Abstract Only).
Sussman et al. "Magnetic Resonance Imaging After Corpus Callosotomy." Neurol. 37:350-354 (1987).
Teva Pharmaceuticals. "ADIPex-PO Prescribing Information." (Jan. 2012).
The Merck Index. Budavari et al., eds. Whitehouse Station, NJ: Merck & Co., Inc. (1996):1151-1152, 2232, 2869, 3167, 3181, 3453, 5895, 7415-7416, and 9931.
The Merck Index. Budavari et al., eds. Whitehouse Station, NJ: Merck & Co., Inc. (1996):187-118, 364, 475, 528-529, 574, 998, 1251-1252, and 1670.
The Merck Index, an Encyclopedia of Chemicals, Drugs, and Biologicals, Twelfth Edition, Published by Merck Research Laboratories (1996).
Third Party Observation filed in European Application No. 09763480.2 dated Nov. 6, 2013.

(56) References Cited

OTHER PUBLICATIONS

Tohen et al. "Two-Year Syndromal and Functional Recovery in 219 Cases of First-Episode Major Affective Disorder with Psychotic Features." Am. J. Psychiatry. 157.2:220-228 (2000).
U.S. Appl. No. 60/121,339, filed Feb. 24, 1999.
U.S. Appl. No. 60/854,756, filed Oct. 27, 2006.
U.S. Appl. No. 61/002,002, filed Nov. 6, 2007.
Vivus, Inc. "QSYMIA.RTM Prescribing Information Sheet." (Apr. 2013).
Weintraub et al. "A Double-Blind Clinical Trial in Weight Control." Arch. Intern. Med. 144:1143-1148 (1984).
Wheatley. "Cellulose, Microcrystalline." Handbook of Pharmaceutical Excipients. Web. (Jan. 2000).
Zarate. "Antipsychotic Drug Side Effect Issues in Bipolar Manic Patients." J. Clin. Psychiatry. 61.3S8:52-61 (2000).

* cited by examiner

ESCALATING DOSING REGIMEN FOR EFFECTING WEIGHT LOSS AND TREATING OBESITY

CROSS-REFERENCE TO RELATED APPLICATIONS

This application is a continuation of U.S. Ser. No. 14/048,416, filed Oct. 8, 2013, which is a continuation of U.S. Ser. No. 12/481,548, filed Jun. 9, 2009, now U.S. Pat. No. 8,580,299, which is a continuation-in-part of U.S. Ser. No. 12/135,953, filed Jun. 9, 2008. The contents of each of these applications are incorporated by reference in their entirety.

BACKGROUND OF THE INVENTION

The prevalence of obesity in both children and adults is on the rise in first world countries, especially in the United States, as well as in many developing countries such as China and India. Many aspects of a person's life are affected by obesity, from physical problems such as knee and ankle joint deterioration, to emotional problems resulting from self-esteem issues and society's attitude towards heavy people. The medical problems caused by obesity can be serious and often life-threatening and include diabetes, shortness of breath and other respiratory problems such as asthma and pulmonary hypertension, gallbladder disease, dyslipidemia (for example, high cholesterol or high levels of triglycerides) and dyslipidemic hypertension, osteoarthritis and other orthopedic problems, reflux esophagitis (heartburn), snoring, sleep apnea, menstrual irregularities, infertility, problems associated with pregnancy, gout, cardiovascular problems such as coronary artery disease and other heart trouble, muscular dystrophy, and metabolic disorders such as hypoalphalipoproteinemia, familial combined hyperlipidemia, and Syndrome X, including insulin-resistant Syndrome X. In addition, obesity has been associated with an increased incidence of certain cancers, notably cancers of the colon, rectum, prostate, breast, uterus, and cervix.

Obesity substantially increases the risk of morbidity from hypertension, dyslipidemia, type II diabetes, coronary heart disease, stroke, gallbladder disease, osteoarthritis and endometrial, breast, prostate, and colon cancers. Higher body weights are also associated with increases in all-cause mortality. Many of these problems are relieved or improved when the afflicted individual undergoes permanent significant weight loss. Weight loss in these individuals can also promote a significant increase in longevity.

Strategies for treating obesity and related disorders have included dietary restriction, increased physical activity, pharmacological approaches, and even surgery, with the choice depending, at least in part, on the degree of weight loss one is attempting to achieve as well as on the severity of obesity exhibited by the subject. For example, treatments such as a low-calorie, low-fat diet and/or regular exercise are often adequate with individuals who are only mildly overweight. The difficulty in maintaining long-term weight loss through diet and behavior modification, however, has led to an increasing interest in other avenues for treatment, particularly pharmacotherapy.

Traditional pharmacological interventions typically induce a weight loss of between five and fifteen kilograms; if the medication is discontinued, renewed weight gain often ensues. Surgical treatments are comparatively successful and are reserved for patients with extreme obesity and/or with serious medical complications.

The above treatments can be enhanced by controlled use of over-the-counter appetite suppressants including caffeine, ephedrine and phenylpropanolamine (Acutrim®, Dexatrim®). Moreover, prescription medications including amphetamine, diethylpropion (Tenuate®), mazindol (Mazanor®, Sanorex®), phentermine (Fastin®, Ionamin®), phenmetrazine (Preludin®), phendimetrazine (Bontrol®, Plegine®, Adipost®, Dital®, Dyrexan®, Melfiat®, Prelu-2®, Rexigen Forte®), benzphetamine (Didrex®) and fluoxetine (Prozac®) are often used in the treatment of seriously overweight and/or obese subjects or patients.

While society has seen tremendous advances in the field of pharmaceuticals, there are, of course, drawbacks to the administration of any given pharmaceutical agent. Sometimes, the disadvantages, or "side effects," are so severe as to preclude administration of a particular agent at a therapeutically effective dose. Furthermore, many agents in the same therapeutic class display similar side effect profiles, meaning that patients either have to forego therapy or suffer from varying degrees of side effects associated with the medication of choice.

The present invention is directed to an escalating dosing regimen for administering topiramate alone or in combination with a second therapeutic agent that directly or indirectly reduces the side effects associated with one or both of the agents administered. By "indirectly" reducing side effects is meant that the second therapeutic agent allows the first pharmaceutical agent to be administered at a lower dose without compromising therapeutic efficacy, thus resulting dose-dependent unwanted effects.

Topiramate (2,3,4,5-bis-O-(1-methylethylidene)-β-D-fructopyranose sulfamate) is a broad-spectrum neurotherapeutic agent approved by the FDA and the regulatory agencies of many other countries for the treatment of certain seizure disorders and the prevention of migraine headaches. E. Faught et al. (1996) Neurology 46:1684-90; Karim et al. (1995) Epilepsia 36 (S4):33; S. K. Sachdeo et al. (1995) Epilepsia 36(S4):33; T. A. Glauser (1999) Epilepsia 40 (S5): S71-80; R. C. Sachdeo (1998) Clin. Pharmacokinet. 34:335-346). There has also been evidence that topiramate is effective in the treatment of diabetes (U.S. Pat. Nos. 7,109,174 and 6,362,220), neurological disorders (U.S. Pat. No. 6,908,902), depression (U.S. Pat. No. 6,627,653), psychosis (U.S. Pat. No. 6,620,819), headaches (U.S. Pat. No. 6,319,903) and hypertension (U.S. Pat. No. 6,201,010). However there have been adverse effects associated with the use of topiramate in humans, such as cognitive dulling and word finding difficulties, which can discourage many obese patients from taking this drug.

As such, there is considerable interest in the development of additional methods and compositions for treating obesity and related conditions in which the therapeutic efficacy of known therapeutic agents and compositions are improved. In addition, combination therapy, wherein two or more active agents are administered in combination, may be employed to decrease the dose of each individual active agent administered and mitigate one or more side effects of the other active agent or agents. Given that the incidence of obesity and conditions caused by or related to obesity has reached epidemic proportions, there is an urgent need for effective methods for the treatment of obesity and/or a related condition, including combination treatments that result in reduction of toxicity, decreased side effects and effective treatment.

SUMMARY OF THE INVENTION

The present invention provides novel topiramate compositions and methods for effecting weight loss, treating obesity, and treating conditions caused by or associated with excess weight or obesity. The compositions can contain topiramate as a single active agent but more typically contain topiramate in combination with at least one sympathomimetic agent. The term "sympathomimetic agent" is a term of art and refers to agents or compounds that mimic or alter stimulation of the sympathetic nervous system. Exemplary sympathomimetic agents include phentermine and bupropion. Optimally, the topiramate and the sympathomimetic agent are contained in a single dosage form, which provides for immediate release of the sympathomimetic agent and controlled release, e.g., sustained release, delayed release, or both sustained release and delayed release, of the topiramate.

In another aspect of the invention, a controlled release topiramate composition is provided that is composed of an effective amount of topiramate, microcrystalline cellulose, and methylcellulose. Such a composition will provide for sustained release of the topiramate. The composition, in the form of, for instance, a bead or tablet, may be coated with ethyl cellulose, polyvinyl pyrrolidone, or the like, to provide for delayed release of the topiramate as well. A sympathomimetic agent is preferably although not necessarily included, and, if present, is preferably in immediate release form.

The present invention features an escalating dosing regimen for administering topiramate alone or in combination with a sympathomimetic agent, wherein the dosing regimen is in the context of a method for effecting weight loss, e.g., in a method for treating obesity, overweight, or a condition associated with obesity, or in an alternative method, e.g., a method for treating epilepsy, a method for treating an impulse control disorder, or the like. The method involves administration of a topiramate composition as described above, wherein the topiramate is generally although not necessarily administered in a controlled release composition and/or in combination with a sympathomimetic agent. The escalating dosing regimen involves administration of an initial daily dosage to an individual for a specific time period and incrementally increasing the dosage at various designated time points.

The invention also provides a packaged pharmaceutical preparation comprising topiramate, optionally a sympathomimetic agent as well, and instructions for administering, e.g., self-administering, the active agent(s). Generally, the instructions for administration include reference to an escalating dosing regimen wherein a lower daily dosage of topiramate is administered initially, with incremental increases at various designated time points thereafter. Ideally, a titration card is provided that sets forth the recommended dosages for at least four weeks.

DETAILED DESCRIPTION OF THE INVENTION

Definitions and Nomenclature

Figure 1:
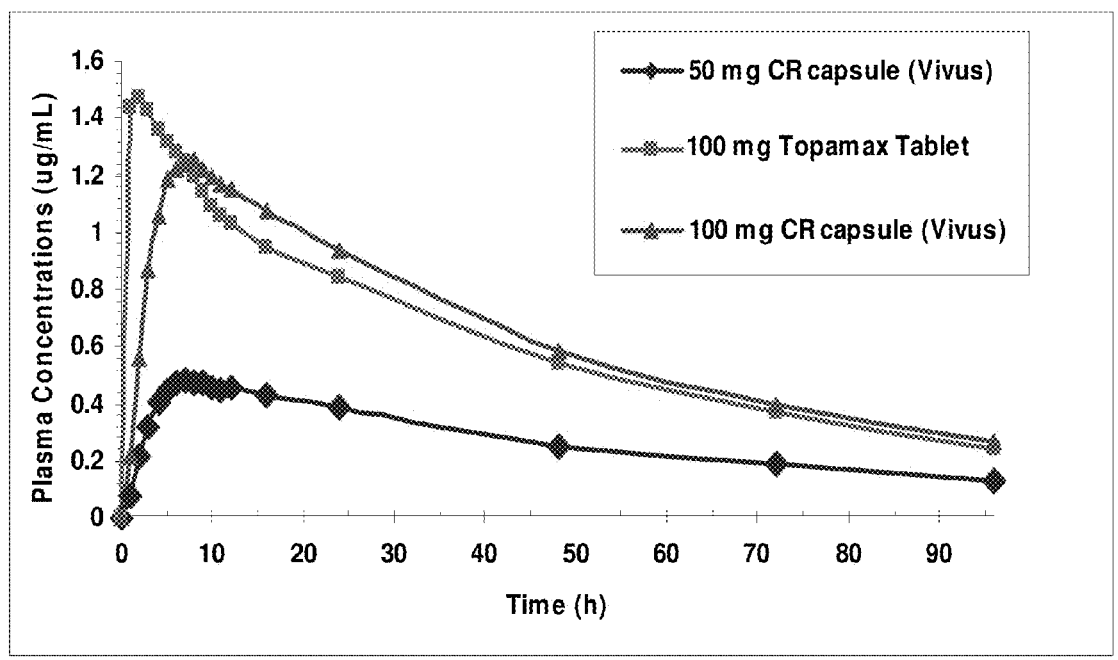
FIG. 1 provides a summary of the plasma concentration of controlled release topiramate according to the present invention versus topiramate (Topamax®) in normal obese subjects.

It must be noted that, as used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

Unless defined otherwise, all technical and scientific terms used herein have the meaning commonly understood by one of ordinary skill in the art to which the invention pertains. Specific terminology of particular importance to the description of the present invention is defined below.

When referring to an active agent, applicants intend the term "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds as will be discussed infra. Therefore, reference to "phentermine," for example, or "bupropion," encompasses not only phentermine and bupropion per se but also salts and other derivatives of phentermine and bupropion, e.g., phentermine hydrochloride and bupropion hydrochloride, respectively. It is to be understood that when amounts or doses are specified, that those amounts or doses refer to the amount or dose of active agent per se and not to a salt or the like. For example, when it is indicated that a dose or amount of phentermine is 7.5 mg, that would correspond to 9.84 phentermine hydrochloride and not 7.5 phentermine hydrochloride.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a subject" refers to the process of introducing a composition or dosage form of the invention into the subject (e.g., a human or other mammalian subject) via an art-recognized means of introduction By the terms "effective amount" and "therapeutically effective amount" of an agent, compound, drug, composition or combination of the invention which is nontoxic and effective for producing some desired therapeutic effect upon administration to a subject or patient (e.g., a human subject or patient).

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release, modified release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient provides a measurable time delay before drug is released from the formulation into the patient's body.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "subject" or "individual" or "patient" refers to any subject for whom or which therapy is desired, and generally refers to the recipient of the therapy to be practiced according to the invention. The subject can be any vertebrate, but will typically be a mammal. If a mammal, the subject will in many embodiments be a human, but may also be a domestic livestock, laboratory subject or pet animal.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and Formulations of the Invention:

The present invention provides novel methods and compositions to effect weight loss and treat obesity, conditions related to excess weight or obesity, diabetes (whether or not related to obesity), and other conditions and disorders as will be explained infra. According to the U.S. Centers for Disease Control, the clinical definition of being overweight (the term being used synonymously herein with the term "excess weight") is having a body mass index (BMI) between 25.0 and 29.9 kg/m; BMI is calculated by multiplying an individual's weight, in kilograms, by height, in meters. The CDC defines obesity as having a BMI of 30 or higher. In one embodiment, the invention provides a method for effecting weight loss and treating overweight, obesity, and conditions associated with excess weight and obesity, and involves administration of a combination of the sympathomimetic agent phentermine and the anti-convulsant agent topiramate.

Topiramate is an anticonvulsant sulfamate compound that is sold in the United States under the trade name Topamax® (Ortho-McNeil Pharmaceutical, Inc., Raritan, N.J., U.S.A). Topiramate has been approved for use as an antiepileptic agent as an adjuvant therapy for patients with partial onset seizures or primary generalized tonic-clonic seizures, and for the prevention of migraine headache. See Physician's Desk Reference, 56th ed. (2002); see also U.S. Pat. No. 4,513,006 to Maryanoff et al. and U.S. Pat. No. 7,351,695 to Almarssoo et al.

"Topiramate" generally refers to the sulfamate-substituted monosaccharide having the chemical name 2,3,4,5-bis-O-(1-methylethylidene)-β-D-fructopyranose sulfamate and the molecular formula C12H21NO8S. The structure of the compound is represented by Formula (I)

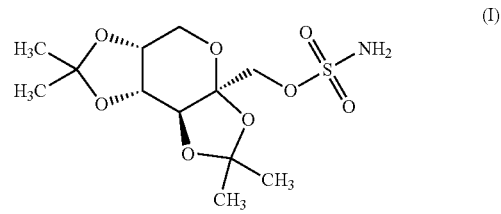 [SMILES: CC1(C)O[C@@H]2[C@@H](CO[C@@]3(COS(N)(=O)=O)OC(C)(C)O[C@@H]23)O1]

As used herein, the term "topiramate" encompasses 2,3,4,5-bis-(O)-(1-methylethylidene)-β-D-fructopyranose sulfamate as well as individual enantiomers, individual diastereomers, or mixtures thereof. The term "topiramate" as used herein also encompasses topiramate salts as well as polymorphs, solvates (including hydrates and mixed solvates, as well as hydrates of salts), co-crystals (for instance, with other compounds or other forms of topiramate), amorphous, and anhydrous forms of the compound of Formula (I). Topiramate salts useful in conjunction with the present invention, as will be appreciated from the fact that the compound is a sulfamic acid derivative, are pharmaceutically acceptable basic addition salts. Such salts are prepared from bases that provide a pharmaceutically acceptable cation that associates with the sulfamic acid group of the compound of Formula (I). Suitable pharmaceutically acceptable cations include both organic and inorganic cations, including, without limitation, sodium, sodium, potassium, lithium, magnesium, calcium, aluminum, zinc, procaine, benzathine, chloroprocaine, choline, diethylamine, ethylenediamine, N-methylglucamine, benethamine, clemizole, diethylamine, piperazine, tromethamine, triethylamine, ethanolamine, triethanolamine, arginine, lysine, histidine, tributylamine, 2-amino-2-pentylpropanol, 2-amino-2-methyl-1,3-propanediol, tris(hydroxymethyl) aminomethane, benzylamine, 2-(dimethylamino)ethanol, barium or bismuth counter ions. Particularly preferred cations are sodium, lithium, and potassium. Other forms of topiramate referenced above may be prepared using methods known in the art; see, e.g., U.S. Pat. No. 7,351,695. The subject methods include a dosing regimen for the administration of topiramate alone or, more preferably, in combination with a sympathomimetic agent. In certain aspects, the present invention provides a dosing regimen for the administration of a pharmaceutical composition that includes, e.g., topiramate in combination with bupropion or phentermine.

In one embodiment of the invention, directed to an escalating dosage regimen, the dosing strategy involves administering to a patient a lower daily dosage of topiramate alone or in combination with a sympathomimetic agent for a specific period of time and then incrementally increasing the dosage at various designated time points.

For example, when treating a patient who is overweight or obese, and who may suffer from a condition associated with or caused by excess weight or obesity, the patient receives a dosage of 15 mg/day to 30 mg/day, e.g., 23 mg/day, of topiramate for 1 week. Next, the patient receives a dosage of 35 mg/day to 55 mg/day, e.g., 46 mg/day, of topiramate for a second week. Thereafter, the patient receives a dosage of 60 mg/day to 80 mg/day, e.g., 69 mg/day, of topiramate for a third week, which is followed by a final dosage of 85 mg to 125 mg/day, e.g., 92 mg/day of topiramate for a fourth week.

In another example, when treating a patient for obesity and/or a related condition, the patient receives a dosage of 15 mg/day to 30 mg/day, e.g., 23 mg/day, of topiramate in combination with a dosage of 3.75 mg/day of phentermine for 1 week. The patient next receives a dosage of 35 mg/day to 55 mg/day, e.g., 46 mg/day, of topiramate in combination with a dosage of 7.5 mg/day of phentermine for a second week. Thereafter, the patient receives a dosage of 60 mg/day to 80 mg/day, e.g., 69 mg/day, of topiramate in combination with a dosage of 11.25 mg/day of phentermine for a third week which is followed by a final dosage of 85 mg/day to 125 mg/day, e.g., 92 mg/day, topiramate in combination with a dosage of 15 mg/day of phentermine for a fourth week.

After the fourth week of administration, the further administration of topiramate alone or topiramate in combination with phentermine is carried on indefinitely or, more typically, until a sufficient reduction of symptoms has been achieved. In certain aspects, the final dose of 92 mg/day of topiramate alone or in combination with a dosage of 15 mg/day of phentermine indefinitely or until a sufficient reduction of symptoms has been achieved. In other aspects, the final dose of topiramate alone or topiramate in combination with phentermine is decreased to the initial starting dose of the regimen and maintained indefinitely or until a sufficient reduction of symptoms has been achieved. In a weight loss regimen, the dosage regimen generally involves continual, i.e., ongoing, administration, over a significant period of time, e.g., in the range of about 4 weeks to about 67 weeks, depending on the severity of an individuals weight problem, the amount of weight that should be lost, and the rate at which weight is lost.

In another embodiment of the invention, topiramate is administered on an ongoing basis, i.e., generally following the escalating dosage regimen described above. In either of these methods, i.e., the escalating dosage regimen or an ongoing maintenance dosage regimen, pharmaceutical compositions are administered that include an effective amount of topiramate as the active agent, wherein an "effective amount" of topiramate is generally an amount that results in a reduction of at least one pathological parameter associated with obesity, excess weight, and/or a related disorder. In the methods of the invention, e.g., in a method for effecting weight loss such as in the treatment of obesity and/or a condition related to obesity, an effective amount of topiramate is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter, e.g., loss of weight, in an individual suffering from obesity, excess weight, and/or a related disorder and not treated with the topiramate compositions.

A suitable daily dose of topiramate is in the range of 10 mg to 1500 mg. For example, 10 mg, 20 mg, 30 mg, 60 mg, 90 mg, 120 mg, 150 mg, 180 mg, 210 mg, 240 mg, 270 mg, 300 mg, 330 mg, 360 mg, 390 mg, 420 mg, 450 mg, 480 mg, 500 mg, 600 mg, 800 mg, 1000 mg, 1200 mg, 1500 mg or the like is administered to a patient as a daily dosage. In another example, 23 mg, 46 mg, 69 mg and 92 mg or the like is administered to a patient as a daily dosage. In some embodiments, the daily dosage of topiramate is in the range of 10 mg to 150. In certain embodiments, the daily dosage of topiramate is in the range of 10 mg to 100 mg. Each of the aforementioned "daily dosages" is generally although not necessarily administered as a single daily dose.

The patient may receive a specific dosage of topiramate over a period of weeks, months, or years, e.g., 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like.

Aspects of the invention provide a topiramate monotherapy or combination therapy in which the subject topiramate formulation is effective when administered at a initial dose as low as 10-23 mg. In certain aspects, the topiramate formulation is effective at a dose of approximately 20 mg. The novel topiramate formulations of the present invention have a lower maximum concentration (Cmax) without decreasing total drug exposure defined by the area under the concentration-time curve (AUC). Further, the novel topiramate formulations of the present invention have a delay in time after administration of a drug when the maximum plasma concentration is reached (Tmax) by six to eight hours. As depicted in FIG. 1, drug exposure as measured by AUC for the control release (CR) formulation capsule is the same as the 100 mg of immediate release topiramate (Topamax®) tablet despite a 20% reduction in the Cmax. Therefore, this formulation is capable of reducing the Cmax which would reduce side effects without compromising the efficacy of the treatment, since the AUC is the same. This reduction in Cmax is preferred as topiramate can be sedating and a delay in the time to reach maximum plasma concentration to the late afternoon or evening time would improve the tolerability of the drug.

As such, the effective amount of topiramate is decreased, thereby further reducing any toxicity or harmful side effects in the patient. The amount of topiramate administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. The optimal amount of the compound that should be administered to the patient in the practice of the present invention will depend on the individual as well as the severity of the individual's symptoms.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). Oral administration and therefore oral dosage forms are generally preferred, and include tablets, capsules, caplets, solutions, suspensions and syrups, and may also comprise a plurality of granules, beads, powders, or pellets that may or may not be encapsulated. Preferred oral dosage forms are capsules and tablets, particularly controlled release capsules and tablets, as noted above.

As noted above, it is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of topiramate, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited earlier herein, which describes materials and methods for preparing encapsulated pharmaceuticals.

Oral dosage forms, whether tablets, capsules, caplets, or particulates, can, if desired, be formulated so as to provide for controlled release of topiramate, and in a preferred embodiment, the present formulations are controlled release oral dosage forms. Generally, the dosage forms provide for sustained release, i.e., gradual, release of topiramate, from the dosage form to the patient's body over an extended time period, typically providing for a substantially constant blood level of the agent over a time period in the range of about 4 to about 12 hours, typically in the range of about 6 to about 10 hours or 6 to about 8 hours. Release of the topiramate may also be delayed; that is, there is a time lag between administration and the start of topiramate release. In this way, for instance, an individual will not experience sleepiness or other side effects of topiramate during the school or work day. Preferred dosage forms thus involve sustained release of the topiramate, delayed release of the topiramate, or both sustained and delayed release of the topiramate.

Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone e.g., Povidone K30, polyvinyl acetate, and ethylene-vinyl acetate copolymer. Preferred sustained release polymers herein include those available as "Methocel" polymers from Dow Chemical, particularly the methylcellulose ether polymers in the Methocel™ A group, having a viscosity grade of about 4,000 cps and a methoxyl content of about 27.5% to 31.5%, e.g., Methocel™ A15LV, Methocel™ A15C, and Methocel™ A4M.

When sustained release preparations are prepared, tablets, granules, powder, capsules, and the like can be produced according to a conventional method after adding excipient, and as necessary, binder, disintegrating agent, lubricant, coloring agent, taste-modifying agent, flavoring agent, and the like. These additives may be ones generally used in the field, and for example, lactose, sodium chloride, glucose, starch, microcrystalline cellulose, and silicic acid as the excipient, water, ethanol, propanol, simple syrup, gelatin solution, hydroxypropyl cellulose, methyl cellulose, ethyl cellulose, shellac, calcium phosphate, and polyvinylpyrrolidone as the binder, agar powder, sodium hydrogen carbonate, sodium lauryl sulfate, and stearic acid monoglyceride as the disintegrating agent, purified talc, stearic acid salt, borax, and polyethylene glycol as the lubricant, β-carotene, yellow iron sesquioxide, and caramel as the coloring agent, and saccharose and orange peel as the taste-modifying agent can be listed as examples. It should be noted that various grades of microcrystalline cellulose are preferred fillers herein, e.g., Avicel® PH101, Avicel® PH102, and Avicel® PH200 (FMC), with particle sizes of about 50 microns, 100 microns, and 190 microns, respectively. Microcrystalline cellulose having a particle size in the range of about 50 microns to 200 microns is preferred herein.

The dosage forms may also be provided with a delayed release coating, e.g., composed of an acrylate and/or methacrylate copolymers. Examples of such polymers are those available under the trade name "Eudragit" from Rohm Pharma (Germany). The Eudragit series E, L, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Other preferred Eudragit polymers are cationic, such as the Eudragit E, RS, and RL series polymers. Eudragit E100 and E PO are cationic copolymers of dimethylaminoethyl methacrylate and neutral methacrylates (e.g., methyl methacrylate), while Eudragit RS and Eudragit RL polymers are analogous polymers, composed of neutral methacrylic acid esters and a small proportion of trimethylammonioethyl methacrylate.

In a specific embodiment, controlled release topiramate beads for oral administration, e.g., by incorporation in an orally administrable capsule or compaction into an orally administrable tablet, are made using an extrusion spheronization process to produce a matrix core comprised of: topiramate, 40.0% w/w; microcrystalline cellulose, e.g., Avicel® PH102, 56.5% w/w; and methylcellulose, e.g., Methocel™ A15 LV, 3.5% w/w. The topiramate cores are then coated with ethyl cellulose, 5.47% w/w and Povidone K30: 2.39% w/w. As will be described in detail infra, beads of a second active agent, e.g., a sympathomimetic agent, may also be prepared and incorporated into the capsule. For instance, phentermine or bupropion beads having an immediate release drug coating on sugar spheres or analogous non-active cores may be employed. Both sets of beads may then be encapsulated into one capsule.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The active agents may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agent may be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, or via an implanted depot, other modes of administration are suitable as well. For example, administration may be transmucosal, e.g., rectal or vaginal, preferably using a suppository that contains, in addition to the active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

In another embodiment, the methods of the invention, i.e., the escalating dosage regimen or ongoing maintenance dosing, involve administration of a combination of topiramate and a sympathomimetic agent.

Sympathomimetic agents for use in the present invention and their general clinical uses or effects are set forth in Table 1.

TABLE 1

Sympathomimetic Agents and Clinical Uses Thereof

| Agent name | Ring substituent(s) | $R^\alpha$ | $R^\beta$ | $R^\gamma$ | α Receptor A N P V | β Receptor B C | CNS, 0 |
|---|---|---|---|---|---|---|---|
| Bupropion | 3-Cl | =O | $CH_3$ | $C(CH_3)_3$ | | | |
| Phenylethylamine | | H | H | H | | | |
| Epinephrine | 3-OH, 4-OH | OH | H | $CH_3$ | A, P, V | B, C | |
| Norepinephrine | 3-OH, 4-OH | OH | H | H | P | | |
| Epinine | 3-OH, 4-OH | H | H | $CH_3$ | | | |
| Dopamine | 3-OH, 4-OH | H | H | H | P | | |
| Dobutamine | 3-OH, 4-OH | H | H | 1* | | C | |
| Nordefrin | 3-OH, 4-OH | OH | $CH_3$ | H | V | | |
| Ethylnorepinephrine | 3-OH, 4-OH | OH | $CH_2CH_3$ | H | | B | |
| Isoproterenol | 3-OH, 4-OH | OH | H | $CH(CH_3)_2$ | | B, C | |

TABLE 1-continued

Sympathomimetic Agents and Clinical Uses Thereof

| | General structure: | | | | Main Clinical Uses | | |
|---|---|---|---|---|---|---|---|
| Agent name | Ring substituent(s) | $R^\alpha$ | $R^\beta$ | $R^\gamma$ | <Receptor A N P V | ® Receptor B C | CNS, 0 |
| Protokylol | 3-OH, 4-OH | OH | H | 2* | | B | |
| Isoetharine | 3-OH, 4-OH | OH | $CH_2CH_3$ | $CH(CH_3)_2$ | | B | |
| Metaproterenol | 3-OH, 5-OH | OH | H | $CH(CH_3)_2$ | | B | |
| Terbutaline | 3-OH, 5-OH | OH | H | $C(CH_3)_3$ | | B | |
| Metaraminol | 3-OH | OH | $CH_3$ | H | P | | |
| Phenylephrine | 3-OH | OH | H | $CH_3$ | N, P | | |
| Tyramine | 4-OH | H | H | H | | | |
| Hydroxyamphetamine | 4-OH | H | $CH_3$ | H | N, P | C | |
| Methoxyphenamine | 2-$OCH_3$ | H | $CH_3$ | $CH_3$ | | B | |
| Methoxamine | 2-$OCH_3$, 5-$OCH_3$ | OH | $CH_3$ | H | P | | |
| Albuterol | 3-$CH_2OH$, 4-OH | OH | H | $C(CH_3)_3$ | | B | |
| Amphetamine | | H | $CH_3$ | H | | | CNS, 0 |
| Methamphetamine | | H | $CH_3$ | $CH_3$ | P | | CNS, 0 |
| Benzphetamine | | H | $CH_3$ | —$NHR^\gamma$ is replaced with 3* | | | 0 |
| Ephedrine | | OH | $CH_3$ | $CH_3$ | N, P | B,C | |
| Phenylpropanolamine | | OH | $CH_3$ | H | N | | |
| Mephentermine | | H | —$CHR^\beta$— is replaced with 4* | $CH_3$ | N, P | | |
| Phentermine | | H | " | H | | | 0 |
| Chlorphentermine | 4-Cl | H | " | H | | | 0 |
| Fenfluramine | 3-$CF_3$ | H | $CH_3$ | $C_2H_5$ | | | 0 |
| Propylhexedrine | 5*: phenyl ring is replaced with cyclohexyl | H | $CH_3$ | $CH_3$ | N | | |
| Diethylpropion | | | 6*: The substituent at the 1-position is replaced with 6, below. | | | | 0 |
| Phenmetrazine | | | 7*: The substituent at the 1-position is replaced with 7, below. | | | | 0 |
| Phendimetrazine | | | 8*: The substituent at the 1-position is replaced with 8, below. | | | | 0 |

*1: 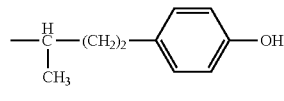  *2: 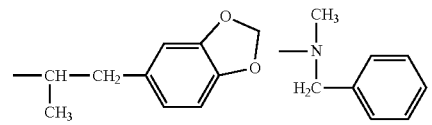  *3: 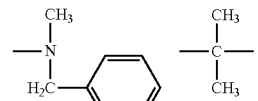  *4: 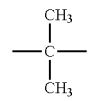

*5:   *6: *7: 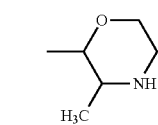

<Activity
A = Allergic reactions (includes ® action)
N = Nasal decongestion
P = Pressor (may include ® action)
V = Other local vasoconstriction (e.g. in local anesthesia)

® Activity
B = Bronchodilator
C = Cardiac

CNS = Central nervous system
0 = Anorectic

*Numbers bearing an asterisk refer to the substituents numbered in the bottom rows of the table; substituent 5 replaces the phenyl rings, and 6, 7 and 8 are attached directly to the phenyl ring, replacing the ethylamine side chain.
†The and ® in the prototype formula refer to positions of the C atoms in the ethylamine side chain.

In certain embodiments, the sympathomimetic agent is phentermine or a phentermine-like compound. As defined herein, a "phentermine-like compound" is a compound structurally related to phentermine (e.g., an analog or derivative) which maintains an anorectic activity similar to that of phentermine. One phentermine-like compound is chlorphentermine. In yet another embodiment, the sympathomimetic agent is amphetamine or an amphetamine-like compound. As used herein, an "amphetamine-like compound" is a compound structurally related to amphetamine (e.g., an analog or derivative) which maintains an anorectic effect of amphetamine. In yet another embodiment, the sympathomimetic agent is phenmetrazine or a phenmetrazine-like compound. As defined herein, a "phenmetrazine-like compound" is a compound structurally related to phenmetrazine (e.g., an analog or derivative) which maintains an anorectic effect of phenmetrazine. One phenmetrazine-like compound is phendimetrazine. Analogs and/or derivatives of the compounds of the present invention can be tested for their ability to suppress appetite (e.g., suppress food intake) in a subject (e.g., a mammalian subject).

In other embodiments, the sympathomimetic agent is bupropion or a bupropion-like compound. As defined herein, a "bupropion-like compound" is a compound structurally related to bupropion (e.g., an analog or derivative) which maintains an anti-depressive activity similar to that of bupropion.

In an exemplary embodiment, the sympathomimetic agent is selected from bupropion, amphetamine, methamphetamine, benzphetamine, phenylpropanolamine, phentermine, chlorphentermine, diethylpropion, phenmetrazine, and phendimetrazine (as set forth in Table 1).

In one embodiment, the sympathomimetic agent is phentermine. It is also within the scope of the present invention to utilize other sympathomimetic agents including pseudoephedrine (a stereoisomer of ephedrine), methylphenidate, dexmethylphenidate, tuaminoheptane, and other CNS stimulants including, for example, caffeine and bupropion.

The selection of appropriate dosages for the drugs used in combination therapy according to the present invention can be determined and optimized by the skilled artisan, e.g., by observation of the patient, including the patient's overall health, the response to the combination therapy, and the like. Optimization may be necessary if it is determined that a patient is not exhibiting the desired therapeutic effect or, conversely, if the patient is experiencing undesirable or adverse side effects that are too many in number or are of troublesome severity.

Although the dosage used will vary depending on the clinical goals to be achieved, a suitable daily dose range for the sympathomimetic agent is generally in the range of 2 mg to 1500 mg, administered to a patient over an ongoing time period. For example, 2 mg, 4 mg, 10 mg, 20 mg, 30 mg, 60 mg, 90 mg, 120 mg, 150 mg, 180 mg, 210 mg, 240 mg, 270 mg, 300 mg, 330 mg, 360 mg, 390 mg, 420 mg, 450 mg, 480 mg, 500 mg, 600 mg, 800 mg, 1000 mg, 1200 mg, 1500 mg or the like is administered to a patient as a daily dosage, which may be a single daily dosage. In another example, 3.75 mg, 7.5 mg, 11.75 mg, 15 mg or the like is administered to a patient as a daily dosage, which, again, may be a single daily dosage.

In one embodiment, each component of the combination (e.g., (i) topiramate, and (ii) a sympathomimetic drug) is prescribed at a dose that is below the typically described dose for each component as a monotherapy. The components may be prescribed separately or as a combination dosage. In one embodiment, each component of the combination (e.g., (i) topiramate, and (ii) a sympathomimetic drug) is prescribed at a dose that is above the typically described dose for each component as a monotherapy. The components may be prescribed separately or as a combination dosage.

In another embodiment, the prescribed dosage of the sympathomimetic drug is above the typically described dose for monotherapy, and topiramate is prescribed at a dosage that is at or below the typically described dose for monotherapy. In another embodiment, the prescribed dosage of the sympathomimetic drug is at or below the typically described dose for monotherapy, and topiramate is prescribed at a dosage that is above the typically described dose for monotherapy.

In certain embodiments, when phentermine is the sympathomimetic agent, phentermine may be, for example, administered at a daily dosage, e.g., a single daily dosage, in the range of 2 mg to 60 mg. In one aspect, the phentermine is administered at a daily dosage, e.g., a single daily dosage, in the range of 2 mg to 30 mg. In another aspect, the phentermine is administered at a daily dosage, e.g., a single daily dosage, in the range of 2 mg to 15 mg.

In certain embodiments, when bupropion is the sympathomimetic agent, bupropion may be, for example, administered at a daily dosage, e.g., a single daily dosage, in the range of 50 mg to 400 mg, more typically in the range of 50 mg to 200 mg.

The method of administration of pharmaceutical combinations of the invention will depend, in particular, on the type of sympathomimetic agent used. Topiramate and the sympathomimetic agent may be administered together in the same composition or simultaneously or sequentially in two separate compositions. Also, one or more sympathomimetic agents may be administered to a subject or patient either in the form of a therapeutic composition or in combination, e.g., in the form of one or more separate compositions administered simultaneously or sequentially. The schedule of administration will be dependent on the type of sympathomimetic agent(s) chosen. For example, a sympathomimetic agent can have a stimulant effect and the degree of the stimulant effect may vary depending on the sympathomimetic agent chosen. A sympathomimetic agent having a significant stimulant effect would preferably be administered earlier in the day than would a sympathomimetic agent having a lesser stimulant effect. Topiramate, which typically has at least some sedative effect even at lower doses, may be administered later in the day than administration of a compound having a lesser sedative effect.

In one embodiment, topiramate is administered in a controlled release form, i.e., in sustained release and/or delayed release form, preferably both, and phentermine is administered in an immediate release form. As such, the phentermine may be taken in the morning because the drug is a stimulant as well as an appetite suppressant. In this embodiment, topiramate may be taken later in the day than the phentermine. Preferably, the patient takes the topiramate just before dinner or later in the evening because the drug is sedating.

In yet another embodiment, topiramate is administered in a controlled release form, i.e., in sustained release and/or delayed release form, and bupropion is administered in an immediate release form. As such, the bupropion may be taken in the morning because the drug is a stimulant as well as an appetite suppressant. In this embodiment, topiramate may be taken later in the day than the bupropion. Preferably, the patient takes the topiramate just before dinner or later in the evening because the drug is sedating.

As described supra, a controlled release dosage form of the invention wherein combination therapy is indicated can be a capsule containing controlled release topiramate beads and immediate release phentermine beads, bupropion beads, or the like. The topiramate beads may be made using an extrusion spheronization process to produce a matrix core comprised of: topiramate, 40.0% w/w; microcrystalline cellulose, e.g., Avicel® PH102, 56.5% w/w; and methylcellulose, e.g., Methocel™ A15 LV, 3.5% w/w. The topiramate cores are then coated with ethyl cellulose, 5.47% w/w and Povidone K30: 2.39% w/w. The phentermine beads, bupropion beads, or the like, are composed of an immediate release drug coating on sugar spheres or analogous non-active cores. Both sets of beads are then encapsulated into one capsule.

In certain embodiments, the phentermine beads may be provided with a controlled release drug coating on sugar spheres or other non-active cores. In other aspects, the phentermine beads may be coated onto the controlled release topiramate beads.

In combination therapy, then, a preferred method of administration involves simultaneous administration of the two active agents, in a single composition or in two discrete compositions each containing one of the active agents. The method of administration may also involve administration of the two active agents at different times of day, with the sympathomimetic agent generally administered earlier in the day and the topiramate generally administered later in the day. Normally, however, the two agents are administered simultaneously using one or more dosage forms that provide for immediate release of the sympathomimetic agent and controlled release of the topiramate. In an exemplary embodiment, the sympathomimetic agent and the topiramate are administered in a single dosage form that provides for immediate release of the sympathomimetic agent and sustained release and/or delayed release, preferably both sustained release and delayed release, of the topiramate. Such dosage forms may be coated cores or encapsulated beads, as described above, or they may be tablets, wherein, for example, the tablets contain at least two discrete segments, at least one of which contains the sympathomimetic agent such as phentermine or bupropion in immediate release form, and another of which contains topiramate in controlled release form.

Indications:

Conditions of particular interest for which the invention finds utility include overweight, obesity and conditions often associated with and/or caused by excess weight and obesity. Topiramate compositions and combinations administered according to the dosage regimens provided herein give rise to significant therapeutic effects and reduced adverse effects, making these pharmaceutical compositions extremely effective therapeutics, especially in the treatment of overweight, obesity and/or related conditions, including conditions associated with and/or caused by excess weight or obesity per se. Subjects suitable for treatment with the subject combination therapy treatment regimen thus include individuals suffering from conditions associated with obesity, such conditions including, without limitation:

diabetes, insulin resistance, and impaired glucose tolerance;

respiratory problems such as pulmonary hypertension, asthma, and shortness of breath;

gallbladder disease;

dyslipidemia, e.g., high cholesterol, high levels of triglycerides, etc.;

osteoarthritis and other orthopedic problems;

reflux esophagitis;

adverse conditions related to sleep, including sleep apnea and loud snoring;

menstrual irregularities, infertility, and complications in pregnancy;

gout;

high blood pressure, i.e., hypertension;

cardiovascular problems such as coronary artery disease and other heart trouble;

muscular dystrophy;

stroke, particularly thrombotic stroke and deep vein thrombosis (DVT);

migraines;

metabolic disorders such as hypoalphalipoproteinemia, familial combined hyperlipidemia, and Syndrome X, including insulin-resistant Syndrome X; and colon, rectal, renal, esophageal, gallbladder, pancreatic, prostate, breast, uterine, ovarian, endometrial, and cervical cancers.

Higher body weights are also associated with increases in all-cause mortality. Most or all of these problems are relieved or improved by permanent significant weight loss. Longevity is likewise significantly increased by permanent significant weight loss.

Diabetes mellitus is very commonly seen in obese individuals, and is associated with continuous and pathologically elevated blood glucose concentration. It is one of the leading causes of death in the United States and is responsible for about 5% of all mortality. Diabetes is divided into two major sub-classes: Type I, also known as juvenile diabetes, or Insulin-Dependent Diabetes Mellitus (IDDM); and Type II, also known as adult onset diabetes, or Non-Insulin-Dependent Diabetes Mellitus (NIDDM).

According to the American Diabetes Association, there are over one million juvenile diabetics in the United States. Type I Diabetes is a form of autoimmune disease. Autoantibodies produced by the patients completely or partially destroy the insulin producing cells of the pancreas. Juvenile diabetics must, therefore, receive exogenous insulin during their lifetime. Without treatment, excessive acidosis, dehydration, kidney damage, and death may result. Even with treatment, complications such as blindness, atherosclerosis, and impotence can occur.

There are more than five million Type II (adult onset) diabetics diagnosed in the United States. Type II disease usually begins during middle age; the principal cause is now known to be overweight and obesity. In Type II diabetics, rising blood glucose levels after meals do not properly stimulate insulin production by the pancreas. Additionally, peripheral tissues are generally resistant to the effects of insulin. The resulting high blood glucose levels (hyperglycemia) can cause extensive tissue damage. Type II diabetics are often referred to as insulin resistant. They often have higher than normal plasma insulin levels (hyperinsulinemia) as the body attempts to overcome its insulin resistance. Some researchers now believe that hyperinsulinemia may be a causative factor in the development of high blood pressure, high levels of circulating low density lipoproteins (LDLs), and lower than normal levels of the beneficial high density lipoproteins (HDLs). While moderate insulin resistance can be compensated for in the early stages of Type II diabetes by increased insulin secretion, in more advanced disease states insulin secretion is also impaired.

Insulin resistance and hyperinsulinemia have also been linked with two other metabolic disorders that pose considerable health risks: impaired glucose tolerance and metabolic obesity. Impaired glucose tolerance is characterized by normal glucose levels before eating, with a tendency toward elevated levels (hyperglycemia) following a meal. According to the World Health Organization, approximately 11% of the U.S. population between the ages of 20 and 74 are estimated to have impaired glucose tolerance. These individuals are considered to be at higher risk for diabetes and coronary artery disease.

Obesity may also be associated with insulin resistance. A causal linkage among obesity, impaired glucose tolerance, and Type II diabetes has been proposed, but a physiological basis has not yet been established. Some researchers believe that impaired glucose tolerance and diabetes are clinically observed and diagnosed only later in the disease process after a person has developed insulin resistance and hyperinsulinemia.

Insulin resistance is frequently associated with hypertension, coronary artery disease (arteriosclerosis), and lactic acidosis, as well as related disease states. The fundamental relationship between these disease states, and a method of treatment, has not been established.

Hypertension is another condition that is frequently seen in obese individuals, and occurs when the blood pressure inside the large arteries is chronically elevated. Hypertension affects about 50 million people in the United States alone. It is more common as people grow older and is both more common and more serious in African Americans. Most cases of hypertension are of unknown etiology. It is known that the tendency to develop hypertension can be inherited. Environment also plays a very important role in hypertension. For example, hypertension may be avoided by keeping body weight under control, keeping physically fit, eating a healthy diet, limiting alcohol intake, and avoiding medications that might increase blood pressure. Other less common causes of hypertension include disorders of the kidneys or endocrine glands. Hypertension has been called "the silent killer" because it has no specific symptoms and yet can lead to death. People with untreated hypertension are much more likely to die from or be disabled by cardiovascular complications such as strokes, heart attacks, heart failure, heart rhythm irregularities, and kidney failure, than people who have normal blood pressure.

Current treatments for hypertension include lifestyle changes (diet, exercise, nonsmoking, etc.) as well as drug therapy. The major classes of medications currently used to treat hypertension include adrenergic neuron antagonists (which are peripherally acting), alpha adrenergic agonists (which are centrally acting), alpha adrenergic blockers, alpha and beta blockers, angiotensin II receptor blockers, angiotensin converting enzyme (ACE) inhibitors, beta adrenergic blockers, calcium channel blockers, thiazides (benzothiadiazine derivatives) and related diuretics, and vasodilators (which act by direct relaxation of vascular smooth muscles).

A particularly serious hypertensive disorder is primary pulmonary hypertension, also known as idiopathic pulmonary hypertension. This is a condition in which the blood pressure in the pulmonary arteries is abnormally high in the absence of other diseases of the heart or lungs. The cause of primary pulmonary hypertension is unknown. Pulmonary hypertension develops in response to increased resistance to blood flow. Narrowing of the pulmonary arterioles occurs and the right side of the heart becomes enlarged due to the increased work of pumping blood against the resistance. Eventually, progressive heart failure develops. Currently, there is no known cure for primary pulmonary hypertension. Treatment is primarily directed towards controlling the symptoms, although some success has occurred with the use of vasodilators. Other medications used to treat the symptoms of primary pulmonary hypertension include diuretics and calcium channel blockers. Typically, as the disease progresses, oxygen is often required. In certain cases, a heart-lung transplant may be indicated for certain suitable candidates, although the availability of donor organs continues to be extremely limited. Unfortunately, primary pulmonary hypertension is a progressive disease, usually leading to congestive heart failure and respiratory failure.

Secondary pulmonary hypertension is a serious disorder that arises as a complication of other conditions such as, for example, scleroderma. Treatments are similar as those for primary pulmonary hypertension and, unfortunately, the prognosis is the same as well.

Other respiratory disorders that are frequently seen in obese individuals include asthma and shortness of breath, both of which conditions are often alleviated by weight loss.

With respect to adverse conditions and disorders associated with sleep, sleep apnea is perhaps the most concerning. Sleep apnea is classified as either obstructive sleep apnea, the more common form that occurs when throat muscles relax, or central sleep apnea, which occurs when the brain doesn't send proper signals to the muscles that control breathing. Additionally, some people have mixed sleep apnea, which is a combination of both obstructive and central sleep apneas. Sleep apnea literally means "cessation of breath." It is characterized by repetitive episodes of upper airway obstruction that occur during sleep, usually associated with a reduction in blood oxygen saturation. In other words, the airway becomes obstructed at several possible sites. The upper airway can be obstructed by excess tissue in the airway, large tonsils, and a large tongue and usually includes the airway muscles relaxing and collapsing when asleep. Another site of obstruction can be the nasal passages. Sometimes the structure of the jaw and airway can be a factor in sleep apnea.

The signs and symptoms of obstructive and central sleep apneas overlap, sometimes making the type of sleep apnea more difficult to determine. The most common signs and symptoms of obstructive and central sleep apneas include: excessive daytime sleepiness (hypersomnia); loud snoring; observed episodes of breathing cessation during sleep; abrupt awakenings accompanied by shortness of breath; awakening with a dry mouth or sore throat; morning headache; and/or difficulty staying asleep (insomnia). Disruptive snoring may be a more prominent characteristic of obstructive sleep apnea, while awakening with shortness of breath may be more common with central sleep apnea.

Sleep apnea is a progressive condition and can be very serious; it is a potentially life-threatening condition that requires immediate medical attention. The risks of undiagnosed obstructive sleep apnea include heart attacks, strokes, high blood pressure, heart disease, irregular heartbeat, and impotence. In addition, obstructive sleep apnea causes daytime sleepiness that can result in accidents, lost productivity and interpersonal relationship problems. The severity of the symptoms may be mild, moderate or severe.

Sleep apnea is diagnosed utilizing a sleep test, called polysomnography but treatment methodologies differ depending on the severity of the disorder. Mild Sleep Apnea is usually treated by some behavioral changes; losing weight and sleeping on one's side are often recommended. There are oral mouth devices (that help keep the airway open) that may help to reduce snoring in three different ways. Some devices (1) bring the jaw forward or (2) elevate the soft palate or (3) retain the tongue (from falling back in the airway and blocking breathing).

Moderate to severe sleep apnea is usually treated with a continuous positive airway pressure (C-PAP). C-PAP is a machine that blows air into your nose via a nose mask, keeping the airway open and unobstructed. For more severe apnea, there is a Bi-level (Bi-PAP) machine. The Bi-level machine is different in that it blows air at two different pressures. When a person inhales, the pressure is higher and in exhaling, the pressure is lower.

Some people have facial deformities that may cause the sleep apnea. It simply may be that their jaw is smaller than it should be or they could have a smaller opening at the back of the throat. Some people have enlarged tonsils, a large tongue or some other tissues partially blocking the airway. Fixing a deviated septum may help to open the nasal passages. Removing the tonsils and adenoids or polyps may help also. Children are much more likely to have their tonsils and adenoids removed. Surgical procedures, such as tracheostomy, uvulopalatopharyngoplasty (UPPP), laser assisted uvuloplasty (LAUP), somnoplasty, and mandibular myotomy are often required to effectively treat sleep apnea. Weight loss, however, particularly in an obese person, can significantly alleviate sleep apnea and other sleep-related adverse conditions such as loud snoring and the like.

Relatively recently, a connection between obesity and the occurrence or increased incidence of migraine headaches has been noted. Migraine headaches begin with mild pain, which increases in intensity over a short period of time. There are two major types of migraines. The common migraine affects 80-85% of migraine sufferers and classical migraine with aura affects 15% of migraine sufferers. Symptoms associated with migraines include headaches, psychological symptomology such as irritability, depression, fatigue, drowsiness, restlessness; neurological symptoms such as photophobia, phonophobia or gastrointestinal symptoms such as change in bowel habit, change of food intake or urinary symptoms such as urinary frequency, auras which are neurological deficits and can be a variety of deficits for the migraine population but in the individual is usually stereotyped. These deficits may be visual scotoma or visual designs, hemiplegia, migrating paraesthesia, dysarthria, dysphasia, or déjà vu. The headache is usually accompanied by light or sound sensitivity, photophobia or phonophobia, irritability and impaired concentration. For those individuals whose migraine headaches are caused by or exacerbated by obesity, treatment according to the methodology of the present invention can be effective.

Other indications for which the present invention is readily adapted include epilepsy and certain psychiatric indications such as impulse control disorders.

Topiramate has long been known as an anti-epileptic agent. At dosages previously required or believed to be required for efficacy, however, topiramate therapy resulted in significant side effects, as noted elsewhere herein. The present invention, according to which topiramate dosage may be reduced by concomitant administration of phentermine, significantly reduces those side effects of topiramate, most if not all of which are dose-related.

Among psychiatric indications, depression is particularly common. "Depression," as is well known, is manifested by a combination of symptoms that interfere with the ability to work, study, sleep, eat, and enjoy once pleasurable activities. Depression includes major depression, especially refractory depression, bipolar depression, and the degeneration associated with depression. Symptoms of depression include persistent sad, anxious, or "empty" mood, feelings of hopelessness, pessimism, feelings of guilt, worthlessness, helplessness, loss of interest or pleasure in hobbies and activities that were once enjoyed, including sex, decreased energy, fatigue, being "slowed down", difficulty concentrating, remembering, making decisions, insomnia, early-morning awakening, or oversleeping, appetite and/or weight loss or overeating and weight gain, thoughts of death or suicide; suicide attempts, restlessness, irritability, persistent physical symptoms that do not respond to treatment, such as headaches, digestive disorders, and chronic pain.

Other psychiatric disorders may also be treated using the compositions and methods of the invention. These disorders include impulse control disorders, panic syndrome, general anxiety disorder, phobic syndromes of all types, mania, manic depressive illness, hypomania, unipolar depression, stress disorders, PTSD, somatoform disorders, personality disorders, psychosis, and schizophrenia.

"Impulse Control Disorders" are characterized by harmful behaviors performed in response to irresistible impulses. The essential feature of an impulse control disorder is the failure to resist an impulse, drive, or temptation to perform an act that is harmful to the person or to others. Symptoms include an increasing sense of tension or arousal before committing an act, and then experiences pleasure, gratification, or release at the time of committing the act. After the act is performed, there may or may not be regret or guilt. Numerous disorders can be characterized as impulse control disorders including intermittent explosive disorder, kleptomania, pathological gambling, pyromania, trichotillomania, compulsive buying or shopping, repetitive self-mutilation, nonparaphilic sexual addictions, severe nail biting, compulsive skin picking, personality disorders with impulsive features, attention deficit/hyperactivity disorder, eating disorders characterized by binge eating, and substance abuse disorders such as alcoholism and drug addiction. Binge eating disorder and bulimia are also sometimes classified as impulse control disorders.

Packaged Pharmaceutical Preparations:

Also provided are packaged pharmaceutical preparations for practicing the subject methods. The packaged preparation contains a composition of the invention in a sealed container, and typically contains a plurality of individual dosage forms each in a sealed housing, as in a blister pack, but could also contain one or more dosage forms in a single sealed container. Optionally, dosage forms with lower doses of one or both active agents can also be included, for dose titration and dose escalation.

In certain embodiments, the packaged pharmaceutical preparations include instructions for a patient to carry out drug administration to achieve weight loss, treat obesity, treat conditions associated with obesity, or treat other conditions as explained earlier herein. For instance, the instructions may include the daily dose of topiramate to be taken, the daily dose of phentermine or other sympathomimetic agent to be taken, and/or the dosing regimen for self-administration of a controlled release dosage form containing topiramate and optionally the second active agent. The instructions may be recorded on a suitable recording medium or printed on a substrate such as paper or plastic. As such, the instructions may be present as a package insert, in the labeling of the package, container(s), or components thereof (i.e., associated with the packaging or sub-packaging), etc. In other embodiments, the instructions are present as an electronic storage data file present on a suitable computer readable storage medium, e.g. CD-ROM, diskette, etc. In yet other embodiments, the actual instructions are not present, but means for obtaining the instructions from a remote source, e.g. via the internet, are provided. As an example, a web address might be included to direct patients to a website where the instructions can be viewed and/or from which the instructions can be downloaded. As with the instructions per se, this means for obtaining the instructions is recorded on a suitable substrate.

Some or all of the included components may be packaged in suitable packaging to maintain sterility. In many embodiments, the components are packaged in a containment element to provide a single, easily handled unit, where the containment element, e.g., box or analogous structure, may or may not be an airtight container, e.g., to further preserve the sterility of some or all of the components. In certain aspects, a sealed package of controlled release dosage forms is provided wherein the dosage forms contain phentermine in immediate release form and topiramate in controlled release, e.g., sustained release and delayed release form. Alternatively, separate phentermine-containing and topiramate-containing dosage forms may be included.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Controlled release topiramate beads are made using an extrusion spheronization process to produce a matrix core comprised of topiramate, 40.0% w/w; microcrystalline cellulose (Avicel® PH102), 56.5% w/w; and Methocel™ A15 LV, 3.5% w/w. The topiramate cores were then coated with ethyl cellulose, 5.47% w/w, and Povidone K30, 2.39% w/w.

The composition of the topiramate beads so prepared is as follows:

| Component | % w/w |
|---|---|
| topiramate | 36.85 |
| microcrystalline cellulose, (Avicel ® PH102) | 52.05 |
| Methylcellulose (Methocel ™ A15 LV) | 3.22 |
| ethylcellulose | 5.47 |
| Polyvinylpyrrolidone (Povidone K30) | 2.39 |

Phentermine hydrochloride was coated onto sugar spheres to provide immediate release phentermine beads. Both sets of beads were then encapsulated into each of a plurality of capsules.

Example 2

Figure 2:
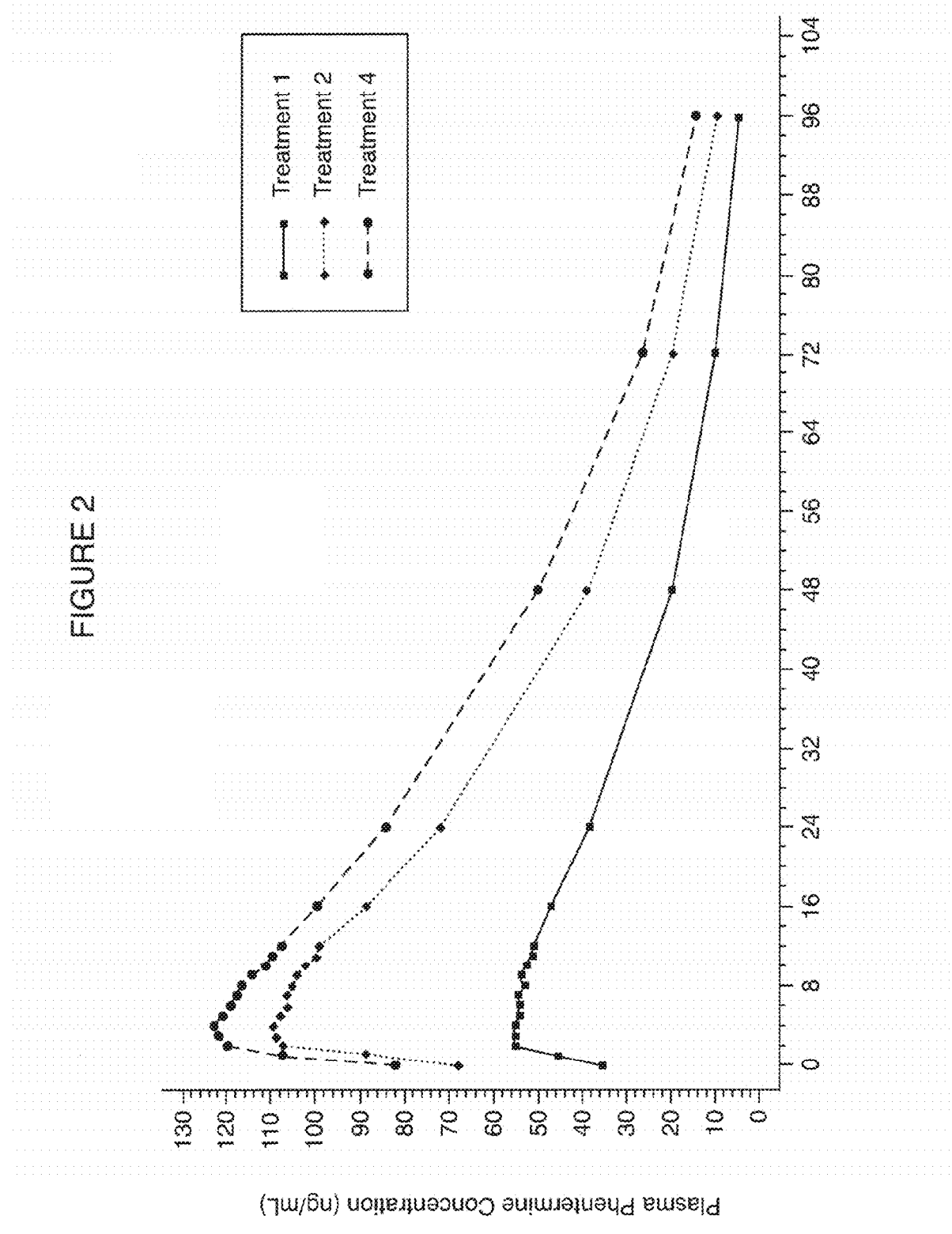
FIG. 2 depicts the mean plasma phentermine concentrations versus time for subjects administered phentermine in combination with controlled release topiramate and phentermine in combination with immediate release topiramate (Topamax®).

In a study comparing controlled-release formulation of topiramate according to the present invention versus immediate release topiramate (Topamax®) in combination with phentermine, the controlled release formulation of the instant invention of topiramate had a 10-15% lower effect on phentermine exposure (FIG. 2).

The mean and statistical comparisons for plasma phentermine PK parameters at steady state in multiple dose administrations are summarized in Table 2.

TABLE 2

Arithmetic Mean (SD) and Statistical Comparison of Pharmacokinetic Parameters for Plasma Phentermine

| Pharmacokinetic Parameters | Mean +/− SD Treatment 2 (N = 13) | Treatment 2 Versus Treatment 4 Treatment 4 (N = 12) | 90% Confidence Intervals | % Mean Ratio |
|---|---|---|---|---|
| $AUC_{0-tau}$ (ng * hr/mL) | 2250 +/− 563 | 2530 +/− 644 | (75.6, 105.3) | 89.2 |
| $AUC_{0-96}$ (ng * hr/mL) | 4640 +/− 1570 | 5550 +/− 1960 | (67.1, 105.0) | 84.0 |
| $AUC_{0-t}$ (ng * hr/mL) | 4640 +/− 1570 | 5550 +/− 1960 | (67.1, 105.0) | 84.0 |
| $C_{max,ss}$ (ng * hr/mL) | 114 +/− 23.6 | 127 +/− 27.6 | (78.8, 104.5) | 90.7 |
| $C_{min,ss}$ (ng * hr/mL) | 9.84 +/− 7.24 | 14.6 +/− 11.3 | (42.5, 109.0) | 68.1 |
| $t_{max}$ (hr) | 4.01 (1.04, 7.00) | 4.54 (1.00, 10.0) | | |
| $T_{1/2}$ (hr) | 23.3 +/− 6.17 | 26.3 +/− 7.43 | | |
| $CL_{ss}/F$ (L/hr) | 7.10 +/− 1.89 | 6.38 +/− 2.00 | | |
| $V_2/F$ (L/hr) | 229 +/− 45.3 | 232 +/− 58.5 | | |

$t_{max}$ is presented as median (minimum, maximum)
Parameters were dose-normalized and ln-transformed prior to analysis.
% Mean Ratio = 100 * ex[(Treatment 2 − Treatment 4) for ln-transformed parameters
Treatment 1 (Test): 7.5 mg phentermine/50 mg topiramate (Formulation A)
Treatment 2 (Test): 15 mg phentermine/100 mg topiramate (Formulation A)
Treatment 4 (Reference): 15 mg phentermine/100 mg topiramate
Source: Tables 14.2.1.8, 14.2.1.10, 14.2.1.12, and 14.2.1.17

These data indicate a lower maximum and extent of phentermine exposure between tests versus reference treatments after multiple-dose administration. As such, the controlled release formulation of topiramate reduced drug interaction with phentermine which in turn will reduce further side effects associated with phentermine.

The invention claimed is:

1. A method for effecting weight loss in a patient having a body mass index of at least 25 kg/m², comprising administering an escalating unit dosage form comprising,
    (a) a first dosage form, comprising,
        23 mg of topiramate, formulated for controlled release, and
        3.75 mg of phentermine, formulated for immediate release,
    wherein the first dosage form is administered to the subject daily for at least 2 weeks; and
    (b) a second dosage form, comprising,
        46 mg of topiramate, formulated for controlled release, and
        7.5 mg of phentermine, formulated for immediate release,
    wherein the topiramate formulated for controlled release reaches maximum plasma concentration (Cmax) at about 6 to about 10 hours (Tmax) after administration.

2. The method of claim 1, wherein the subject has a body mass index between 25 kg/m² and 29.9 kg/m².

3. The method of claim 2, wherein the subject has a condition associated with obesity.

4. The method of claim 1, wherein the subject has a body mass index of at least 30 kg/m².

5. The method of claim 3, wherein the condition associated with obesity is selected from the group consisting of diabetes, elevated fasting blood glucose, insulin resistance, impaired glucose tolerance, pulmonary hypertension, asthma, shortness of breath, gallbladder disease, dyslipidemia, high cholesterol, high levels of triglycerides, osteoarthritis, reflux esophagitis, sleep apnea, menstrual irregularities, infertility, complications in pregnancy, gout, high blood pressure, hypertension, coronary artery disease, heart disease, muscular dystrophy, stroke, thrombotic stroke, deep vein thrombosis (DVT), migraines, metabolic disorders, hypoalphalipoproteinemia, familial combined hyperlipidemia, Syndrome X, insulin-resistant Syndrome X, colon cancer, rectal cancer, renal cancer, esophageal cancer, gallbladder cancer, pancreatic cancer, prostate cancer, breast cancer, uterine cancer, ovarian cancer, endometrial cancer, and cervical cancer.

6. The method of claim 3, wherein the condition associated with obesity is selected from the group consisting of hypertension, dyslipidemia, and type 2 diabetes mellitus.

7. The method of claim 5, wherein the condition associated with obesity is selected from the group consisting of high blood pressure, high levels of triglycerides, elevated fasting blood glucose, and diabetes.

8. The method of claim 3, wherein the subject is suffering from at least two conditions associated with obesity selected from the group consisting of high blood pressure, high levels of triglycerides, elevated fasting blood glucose, and diabetes.

9. The method of claim 3, wherein the subject is suffering from at least two conditions associated with obesity selected from the group consisting of hypertension, dyslipidemia, and type 2 diabetes mellitus.

10. The dosage form of claim 1, wherein the topiramate formulated for controlled release further exhibits a lower Cmax, than non-controlled release topiramate, without decreasing total drug exposure defined by the area under the concentration-time curve (AUC).

11. The method of claim 1, wherein the 3.75 mg phentermine is provided in the first dosage form as about 4.92 mg phentermine hydrochloride, and wherein 4.92 mg of phentermine hydrochloride provides 3.75 mg of phentermine.

12. The method of claim 1, wherein the 7.5 mg phentermine is provided in the second dosage form as about 9.84 mg phentermine hydrochloride, and wherein 9.84 mg of phentermine hydrochloride provides 7.5 mg of phentermine.

13. The method of claim 1, wherein the topiramate formulated for controlled release reaches maximum plasma concentration (Cmax) at a time (Tmax) that is delayed by about 6 to about 8 hours compared to the Tmax of non-controlled release topiramate and exhibits a lower Cmax than non-controlled release topiramate.

14. The method of claim 1, wherein the topiramate formulated for controlled release is formulated for sustained release, delayed release, or both.

15. The method of claim 1, wherein the escalating unit dosage form is formulated for oral administration.

16. The method of claim 1, wherein the weight loss is effective to achieve a reduction of at least about 10% of body weight.

17. A method for effecting weight loss in a patient having a body mass index of at least 25 kg/m$^2$, comprising administering an escalating unit dosage form comprising,
 (a) a first dosage form, comprising,
  23 mg of topiramate, formulated for controlled release, and
  3.75 mg of phentermine, formulated for immediate release,
  wherein the first dosage form is administered to the subject daily for at least 2 weeks; and
 (b) a second dosage form, comprising,
  92 mg of topiramate, formulated for controlled release, and
  15 mg of phentermine, formulated for immediate release,
  wherein the topiramate formulated for controlled release reaches maximum plasma concentration (Cmax) at about 6 to about 10 hours (Tmax) after administration.

18. The method of claim 17, wherein the subject has a body mass index between 25 kg/m$^2$ and 29.9 kg/m$^2$.

19. The method of claim 18, wherein the subject has a condition associated with obesity.

20. The method of claim 17, wherein the subject has a body mass index of at least 30 kg/m$^2$.

21. The method of claim 19, wherein the condition associated with obesity is selected from the group consisting of diabetes, elevated fasting blood glucose, insulin resistance, impaired glucose tolerance, pulmonary hypertension, asthma, shortness of breath, gallbladder disease, dyslipidemia, high cholesterol, high levels of triglycerides, osteoarthritis, reflux esophagitis, sleep apnea, menstrual irregularities, infertility, complications in pregnancy, gout, high blood pressure, hypertension, coronary artery disease, heart disease, muscular dystrophy, stroke, thrombotic stroke, deep vein thrombosis (DVT), migraines, metabolic disorders, hypoalphalipoproteinemia, familial combined hyperlipidemia, Syndrome X, insulin-resistant Syndrome X, colon cancer, rectal cancer, renal cancer, esophageal cancer, gallbladder cancer, pancreatic cancer, prostate cancer, breast cancer, uterine cancer, ovarian cancer, endometrial cancer, and cervical cancer.

22. The method of claim 19, wherein the condition associated with obesity is selected from the group consisting of hypertension, dyslipidemia, and type 2 diabetes mellitus.

23. The method of claim 21, wherein the condition associated with obesity is selected from the group consisting of high blood pressure, high levels of triglycerides, elevated fasting blood glucose, and diabetes.

24. The method of claim 19, wherein the subject is suffering from at least two conditions associated with obesity selected from the group consisting of high blood pressure, high levels of triglycerides, elevated fasting blood glucose, and diabetes.

25. The method of claim 19, wherein the subject is suffering from at least two conditions associated with obesity selected from the group consisting of hypertension, dyslipidemia, and type 2 diabetes mellitus.

26. The dosage form of claim 17, wherein the topiramate formulated for controlled release further exhibits a lower Cmax, than non-controlled release topiramate, without decreasing total drug exposure defined by the area under the concentration-time curve (AUC).

27. The method of claim 17, wherein the 3.75 mg phentermine is provided in the first dosage form as about 4.92 mg phentermine hydrochloride, and wherein 4.92 mg of phentermine hydrochloride provides 3.75 mg of phentermine.

28. The method of claim 17, wherein the topiramate formulated for controlled release reaches maximum plasma concentration (Cmax) at a time (Tmax) that is delayed by about 6 to about 8 hours compared to the Tmax of non-controlled release topiramate and exhibits a lower Cmax than non-controlled release topiramate.

29. The method of claim 17, wherein the topiramate formulated for controlled release is formulated for sustained release, delayed release, or both.

30. The method of claim 17, wherein the escalating unit dosage form is formulated for oral administration.

31. The method of claim 17, wherein the weight loss is effective to achieve a reduction of at least about 10% of body weight.

* * * * *

UNITED STATES PATENT AND TRADEMARK OFFICE
CERTIFICATE OF CORRECTION

PATENT NO.       : 9,011,906 B2
APPLICATION NO.  : 14/495250
DATED            : April 21, 2015
INVENTOR(S)      : Thomas Najarian et al.

It is certified that error appears in the above-identified patent and that said Letters Patent is hereby corrected as shown below:

Specification
At column 4 line 27 "9.84" should be "9.33"
Claims
At column 25 line 22 claim 10 "dosage form" should be "method"
At column 25 line 28 claim 11 "4.92" should be "4.67"
At column 25 line 29 claim 11 "4.92" should be "4.67"
At column 25 line 32 claim 12 "9.84" should be "9.33"
At column 26 line 42 claim 26 "dosage form" should be "method"
At column 26 line 49 claim 27 "4.92" should be "4.67"

Signed and Sealed this
Second Day of February, 2016

Michelle K. Lee
*Director of the United States Patent and Trademark Office*

UNITED STATES PATENT AND TRADEMARK OFFICE
CERTIFICATE OF CORRECTION

PATENT NO.        : 9,011,906 B2           Page 1 of 1
APPLICATION NO.   : 14/495250
DATED             : April 21, 2015
INVENTOR(S)       : Thomas Najarian et al.

It is certified that error appears in the above-identified patent and that said Letters Patent is hereby corrected as shown below:

Claims
At column 25 line 33 claim 12 "9.84" should be "9.33"
At column 26 line 48 claim 27 "4.92" should be "4.67"

Signed and Sealed this
Seventeenth Day of May, 2016

Michelle K. Lee
*Director of the United States Patent and Trademark Office*